(12) United States Patent
Chambers

(10) Patent No.: US 10,302,318 B1
(45) Date of Patent: May 28, 2019

(54) RECURSIVE MULTI-TIERED HEALTH ISOLATION FACILITY

(71) Applicant: Anita Margarette Chambers, Cheyenne, WY (US)

(72) Inventor: Anita Margarette Chambers, Cheyenne, WY (US)

( * ) Notice: Subject to any disclaimer, the term of this patent is extended or adjusted under 35 U.S.C. 154(b) by 0 days.

(21) Appl. No.: 14/839,910

(22) Filed: Aug. 28, 2015

Related U.S. Application Data

(60) Provisional application No. 62/043,271, filed on Aug. 28, 2014.

(51) Int. Cl.
| | |
|---|---|
| *F24F 3/16* | (2006.01) |
| *A61G 10/00* | (2006.01) |
| *F24F 11/00* | (2018.01) |
| *A61G 3/00* | (2006.01) |
| *A61L 9/20* | (2006.01) |

(52) U.S. Cl.
CPC .............. *F24F 3/161* (2013.01); *A61G 3/008* (2013.01); *A61G 10/005* (2013.01); *A61L 9/20* (2013.01); *F24F 11/0001* (2013.01); *F24F 2003/1614* (2013.01); *F24F 2003/1667* (2013.01)

(58) Field of Classification Search
CPC ....... A61G 10/00; A61G 10/005; F24F 3/161; F24F 3/16; F24F 3/044; F24F 2011/0004; F24F 2011/0005; Y10S 55/35
USPC ........ 55/385.2, 471, 473, DIG. 35; 422/121; 454/187, 252, 158; 95/273; 96/15
See application file for complete search history.

(56) References Cited

U.S. PATENT DOCUMENTS

| | | | | |
|---|---|---|---|---|
| 3,107,974 A | * | 10/1963 | Potapenko | F24F 3/16 |
| | | | | 128/898 |
| 3,505,989 A | * | 4/1970 | Truhan | A61G 10/005 |
| | | | | 219/400 |
| 3,601,031 A | * | 8/1971 | Abel | A61G 10/005 |
| | | | | 454/187 |
| 4,129,122 A | * | 12/1978 | Dout | A61G 10/02 |
| | | | | 454/188 |
| 4,409,889 A | * | 10/1983 | Burleson | F24F 3/161 |
| | | | | 454/187 |
| 4,489,881 A | * | 12/1984 | Dean | F24F 3/044 |
| | | | | 236/49.1 |

(Continued)

*Primary Examiner* — Duane Smith
*Assistant Examiner* — Minh Chau T Pham
(74) *Attorney, Agent, or Firm* — Chris J. Zhen

(57) ABSTRACT

A recursive multi-tiered health isolation facility having multiple tiers of facility types. Each facility type has a probability of containing an airborne infectious contagion and a means for provide pressure differentials between the facilities types. Increasingly higher negative pressurization within facility types with a higher probability of airborne infection provides for nesting facility types and abatement of airborne contagions transmitted between facility types. Further, the air exchange rates for each facility type are increased as the probability that a facility type has an airborne infectious agent increases. The use of HEPA filters with the increased air exchange rates increases the contagion abatement in environments having a higher probability of airborne contagions. Further, exchanged air is treated with ultraviolet light to kill contagions making it through the air filter. Additionally, bathroom facilities provided as part of the patient facilities can be coupled to an autoclave incineration facility to prevent contagion contamination by bodily fluids.

17 Claims, 3 Drawing Sheets

(56) References Cited

U.S. PATENT DOCUMENTS

| | | | | |
|---|---|---|---|---|
| 4,850,268 A | * | 7/1989 | Saito | B01L 9/54 422/187 |
| 4,895,171 A | | 1/1990 | Onik | |
| 5,004,483 A | * | 4/1991 | Eller | B08B 15/026 134/111 |
| 5,074,894 A | * | 12/1991 | Nelson | A61G 10/005 422/121 |
| 5,099,751 A | * | 3/1992 | Newman | A62B 3/00 454/187 |
| 5,533,305 A | * | 7/1996 | Bielecki | A61L 2/022 297/343 |
| 5,626,820 A | * | 5/1997 | Kinkead | A61L 9/046 422/122 |
| 5,730,765 A | * | 3/1998 | Henry | B01L 1/02 454/184 |
| 6,308,660 B1 | | 10/2001 | Coiro, Sr. et al. | |
| 6,632,260 B1 | | 10/2003 | Siemers et al. | |
| 6,966,937 B2 | | 11/2005 | Yachi et al. | |
| 6,969,346 B2 | | 11/2005 | Perlatti | |
| 7,217,186 B2 | | 5/2007 | Basset et al. | |
| 7,479,103 B2 | | 1/2009 | Ellen | |
| 7,503,890 B2 | | 3/2009 | Kubicsko et al. | |
| 7,854,229 B2 | | 12/2010 | Sadir et al. | |
| 7,934,981 B2 | | 5/2011 | Muggah | |
| 9,671,985 B2 | | 6/2017 | Ito | |
| 2003/0110946 A1 | * | 6/2003 | Lehman | B01D 46/42 95/273 |
| 2007/0039294 A1 | * | 2/2007 | Airey | B01L 1/50 55/385.2 |
| 2007/0089383 A1 | * | 4/2007 | Spengler | F24F 3/161 55/385.2 |
| 2008/0196367 A1 | * | 8/2008 | Ryder | G01N 1/2226 55/385.2 |
| 2008/0282652 A1 | * | 11/2008 | Wardlaw | B23K 9/321 55/385.2 |
| 2010/0047115 A1 | * | 2/2010 | Krichtafovitch | A61L 9/16 422/4 |
| 2013/0061567 A1 | * | 3/2013 | Kawasaki | B01L 1/04 55/385.2 |
| 2013/0109291 A1 | * | 5/2013 | Holtz | B01L 1/04 454/187 |

\* cited by examiner

RECURSIVE MULTI-TIERED HEALTH ISOLATION FACILITY

CROSS REFERENCE TO OTHER APPLICATIONS

This application claims priority under 35 U.S.C. § 119(e) of the U.S. provisional patent application Ser. No. 62/043,271 filed on Aug. 28, 2014 entitled "Recursive Multi-tiered Health Isolation Facility" The provisional patent application Ser. No. 62/043,271 filed on Aug. 28, 2014 entitled "Recursive Multi-tiered Health Isolation Facility" is hereby incorporated by reference in its entirety.

FIELD OF INVENTION

The present invention is in the technical field of facilities. More particularly, the present invention is in the technical field of health isolation facilities.

INVENTION BACKGROUND

It is common practice to isolate healthcare patients within specialized isolation facilities when they have been exposed to highly infectious diseases. These patients may have been exposed, but not yet confirmed to have the disease, or they may have already been confirmed as having the disease. Such infectious diseases could be transmitted through the air, through bodily fluids, or through other modes of transmission. In each of these cases, and for other cases, patient isolation within an Airborne Infection Isolation (AII) Room is considered standard of care. There is a tremendous need for new systems and facilities that control airborne spread of contagions and provide protection of medical personal within patient isolation facilities.

Throughout the world, various organizations such as the Facility Guidelines Institute (FGI), the American Institute of Architects (AIA), and others have identified building and facilities requirements that must be incorporated into these Airborne Infection Isolation Rooms. These building requirements have been adopted by healthcare licensure and certification organizations such as the Centers for Medicare and Medicaid Services (CMS), The Joint Commission for Accreditation Healthcare Certification (JCAHO); and must be met to license the facility to operate or certify the facility for governmental and insurance reimbursement of healthcare procedures.

The building requirements for an Airborne Infection Isolation (AII) Room are identified in the Facility Guidelines Institute (FGI) "Guidelines for Design and Construction of Health Care Facilities." The specific ventilation requirements are identified in the ANSI/ASHRAE/ASHE"Standard 170 Ventilation of Health Care Facilities."

The general guidelines for Airborne Infection Isolation (AII) Rooms include the capacity of one patient within a single room; a hand washing station within each patient room; an area for gowning and storage of clean and soiled materials shall be located either directly inside or outside of the patient room; a separate room with a toilet, bathtub or shower, and hand washing station shall be provided for each Airborne Infection Isolation (AII) Room.

Architectural details include Airborne Infection Isolation (AII) Room perimeter walls, ceilings, and floors including penetrations shall be sealed. Airborne Infection Isolation (AII) Room doors shall have self-closing devices on all room exit doors; doors shall have edge seals; and window treatments shall be selected for ease of cleaning.

Specific ventilation requirements for Airborne Infection Isolation (AII) Rooms include a negative pressure relationship to adjacent rooms and a permanently installed monitoring device to identify the differential pressure. The Airborne Infection Isolation (AII) Room must also provide a minimum of two outdoor air changes per hour and a total of 12 air changes per hour; all room air shall exhaust directly to the outdoors or be recirculated by means of room units only after passing through a HEPA filtration system. Additionally, the Airborne Infection Isolation (AII) Room shall be designed for a maximum relative humidity of 60% and an air temperature between 70-75 degrees Fahrenheit (21-24 degrees Celsius).

Airborne Infection Isolation (AII) Rooms meeting the requirements listed above have been utilized successfully to isolate patients with infectious diseases including, but not limited to tuberculosis, smallpox virus, swine flu virus, avian flu virus, SARS, and others. However, the use of these types of Airborne Infection Isolation (AII) Rooms has not proven effective at isolating patients with highly infectious diseases such as, but not limited to Ebola virus, Marburg virus, methicillin resistant *staphylococcus aureus* (MRSA), rotavirus, noroviruses and hemorrhagic fever viruses; nor can they be easily deployed in real-world field environments where epidemic and pandemic outbreaks of such diseases occur.

Airborne Infection Isolation (AII) Rooms have been around for decades. However, what is needed are facilities that provide for the needs of the medical personal and provide Airborne Infection Isolation Rooms effective against the highly contagious (infectious) diseases including but not limited to Ebola and Marburg virus, methicillin resistant *staphylococcus aureus* (MRSA), rotavirus, noroviruses and hemorrhagic fever viruses. Further, what is needed are facilities that are easily deployed in real-world field environments where epidemic and pandemic outbreaks of such diseases occur.

SUMMARY OF INVENTION

Figure 1:
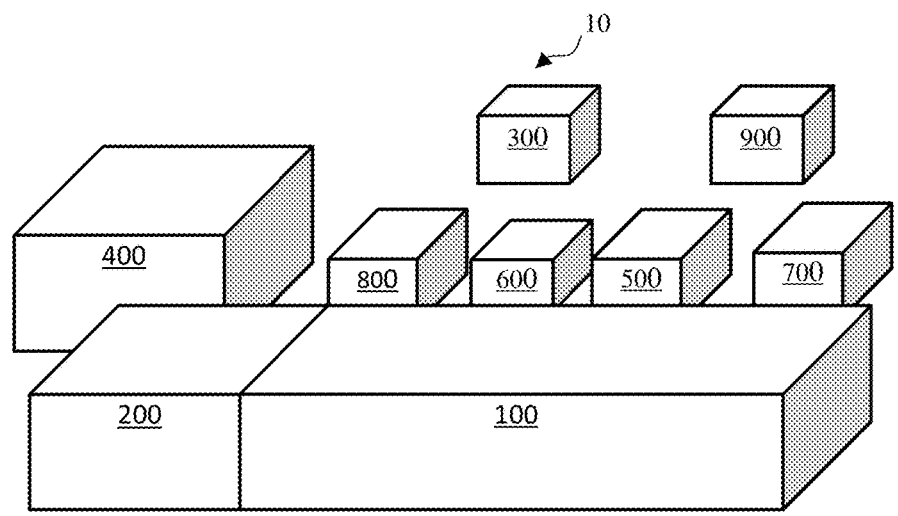
FIG. 1 is a perspective view of the facility of an embodiment of the invention.

The present invention is a recursive multi-tiered patient isolation facility used for the purpose of isolating patients suffering from highly contagious (infectious) communicable diseases from potential patients and medical personal. The isolation facility is comprised of a plurality of connected facility types. Each facility type has a different probability of containing an airborne infection contadgion. A means of providing a negative air-pressure differential is provided between each facility type having a higher probability of airborne contagion.

Additionally, a ventilation system for each facility type has a higher recirculation rate in facilities with a higher probability of airborne contagions. A medical staff facility has the lowest probability of airborne contagions and is kept at a positive pressure relative to the external environment. As part of the ventilation system a HEPA filter filters the recirculating air to each facility type. Further, the ventilation system can include ultraviolet lights to neutralize any contagions that make it past or through the HEPA filter. The present invention can be a fixed structure, can be portable, or can be utilized in part or in whole within an existing or new facility; and it can be rapidly deployed to real-world field environments in cases of emergency or disaster scenarios and to provide an epidemic and pandemic disease patient isolation facility. The complete recursive multi-tiered health isolation facility includes a nested patient isolation facility, a medical staff facility, a gross decontamination facility, a technical decontamination facility, a power generation facility, and a waste management facility capable of inactivating highly contagious (infectious) disease contaminants.

DETAILED DESCRIPTION OF THE INVENTION

The following description of the invention is provided as an enabling teaching of the invention. Those skilled in the relevant art will recognize that many changes can be made to the embodiment described, while still attaining the beneficial results of the present invention. It will also be apparent that some of the desired benefits of the present invention can be attained by selecting some of the features of the present invention without utilizing other features. Accordingly, those skilled in the art will recognize that many modifications and adaptations to the present invention are possible and can even be desirable in certain circumstances, and are a part of the present invention. Thus, the following description is provided as illustrative of the principles of the present invention and not a limitation thereof.

A central feature of the invention is the recursive control of the pressure differentials between different connected facility types where air and/or fluid can leak from one facility type to another and cause the spread of an airborne contagion. Even in a well-designed facility, air and/or fluid can leak through walls and doors and carry with them airborne contagions. To minimize or prevent the movement of an airborne contagion from areas likely to have more airborne contagions to areas less likely to have airborne contagions, facility pressure differentials are used to prevent air flow between these facilities. Differential pressure between facility types that contain, or could contain an airborne contagion and a connected facility type that is not likely or less likely to contain an airborne contagion have a minimum of −0.0.1 inch water column (in. wc), which is equivalent to −2.5 Pascals.

Exemplar of facility types within a multi-tiered health isolation facility include but are not limited to a medical staff facility, medical staff personal protective equipment (PPE), an anteroom, a personal protective equipment (PPE) donning facility, a personal protective equipment (PPE) doffing facility, a suspected infected patient facility, an individual patient isolation facility, an infected patient facility, a suspected infected patient transportation facility, an infected patient transportation facility, a laboratory facility, a contaminated waste holding facility, a contaminated equipment holding facility, a gross decontamination facility, a technical decontamination facility, a contaminated waste processing facility, a suspected infected patient transportation vehicle, and an infected patient transportation vehicle. The pressure differential between facilities is chosen to prevent airborne contagions from moving from an area more likely to have airborne contagions to an area less likely to have airborne contagions.

Directly correlated with the likelihood of airborne contagions is the likelihood of a person contracting the airborne contagion. Within the contagious (infectious) patient facility, the patient(s) already have a contagious disease so any leakage into the facility of air or fluids containing the contagion would be reaching already infected patients. Thus, this sort of leakage is not an issue.

A suspected infected patient facility has the possibility that patients are generating airborne contagions through breathing or epithelial cells (particles of skin) that may be flaking off, as well as contagions in bodily fluids being produced by the patient. Medical personal in this facility should be wearing personal protective equipment (PPE). In such a facility, the facility air pressure should be greater than an adjacent contagious patient facility but less than any coupled facilities that would at any time contain non-infected people without personal protective equipment (PPE). This would include the medical staff facility.

The medical staff facility is an area that is the least likely to contain airborne contagions. The medical personal work in this area without patients and can use the area for any work related duty as well as resting and eating. The medical personal operating in this facility typically do not wear personal protective equipment (PPE). Thus, the highest relative pressure differential is found in the medical staff facility to prevent infiltration of airborne contagions from the other facility types.

Preferably, a positive pressure relative to the surrounding facilities and the atmospheric pressure is used in the medical staff facility. This provides additional benefits. First, the environmental air used to pressurize the medical staff facility is filtered through HEPA filters. Such isolation facilities can be located in an area where there has been an outbreak of a contagious (infectious) airborne disease which could mean that the outside air in that location could contain airborne contagions. By using a positive pressure in the medical staff facility, not only are contagions in the environment kept out, but also the positive pressure keeps out any contagions from the patient facilities having or potentially having airborne contagions.

This recursive use of having a negative pressure differential between a facility type with a higher probability of having airborne contagions than an adjacent facility type with a lower probability of having airborne contagions minimizes or eliminates the probably that airborne contagions leak through the walls or other structures into an area where an uninfected person is found. For example, an infected patient facility has the highest probability of airborne contagions. This is especially true for patients with Ebola. Thus, the infected patient environment should have the lowest air pressure.

Next to, coupled to, or partially/fully surrounding the infected patient facility, can be the suspected infected patient facility. Patients here may have a contagion and may be emitting some airborne contagions. However, these patients are only in this area while being diagnosed and the medical personal should be utilizing personal protective equipment (PPE). The higher pressure in this facility than in the contagious patient facility will prevent contagions from entering from the contagious patent facility.

The means for creating an air and/or fluid pressure differential between a facility type and another facility type can be by any containment material capable of creating or maintaining a differential pressure, fans, pumps, or any other industry standard means for creating both positive and negative pressure room environments. One skilled in the art of designing ventilation systems, water containment systems, and medical environment medical systems would know how to design these systems.

Another aspect of the invention that abates the spread of airborne contagions is to use higher air changes per hour (ACH) rates in facilities more likely to have airborne contagions. The more likely that there is an airborne contagion, the higher the air changes per hour (ACH) of facility air either through the introduction of outdoor air, recirculation through HEPA filters, or a combination thereof. The ACH rate is the number of times per hour that the volume of air in the room passes through the room ventilation system and is replaced by either new outdoor air, recirculated air that has passed through a HEPA filter, or a combination thereof. Thus, an infected patient facility would have the highest ACH rate. Preferably, an ACH rate of greater than twenty times per hour is used. For a suspected infected patient facility, the ACH rate is lower, preferably between twelve and twenty times per hour. For the medical staff facilities, the ACH rate can be the lowest; preferably twelve times per hour or greater.

Another aspect of the multi-tiered facilities configuration that abates airborne contagions is the configuration of the facilities ventilation systems. HEPA filters will remove most contagions passing though the ventilation system but there is the possibility of a defect in the filter or that the virus is too small for the HEPA filter. As a secondary backup, lights that emit ultraviolet radiation can be placed within the recirculation path of the ventilation system to destroy any viruses or contagions that make it past the HEPA filter. One skilled in the art of sterilizing medical facilities or equipment with ultraviolet light radiation would be able to select the intensity of the light to sterilize the ventilation recirculation flow for a given air changes per hour (ACH) rate.

The last abatement feature of the facilities ventilation systems is that the ventilation system for the medical staff facility is separate and unconnected with the patient's facilities or other facilities that are more likely to have airborne contagions. Thus, any problems with the HEPA filters, or the ultraviolet light for the patent facilities or the decontamination facilities will not result in unprotected medical staff being exposed to airborne contagions.

Referring to one embodiment of the invention, FIG. 1 shows a perspective exterior view of a multi-tiered patient isolation facility 10. The facility is comprised of various facility types including but not limited to a patient facility 100, a medical staff facility 200, an optional gross decontamination facility 300, an optional technical decontamination facility 400, an optional waste management system 500, an optional water holding tank 600, an optional sewer holding tank 700, an optional power generator 800, or a vehicle patient isolation facility including but not limited to an patient isolation ambulance, boat, or truck.

While the facilities types 100, 200, 300, 400 are shown in one configuration, FIG. 1, other configurations are contemplated including but not limited to the facilities types 100, 200, 300, 400 located within other facilities 100, 200, 300, 400; facilities 100, 200, 300, 400 adjacent to other facilities 100, 200, 300, 400; facilities 100, 200, 300, and 400 coupled to other facilities 100, 200, 300, 400, or a combination thereof.

Figure 2:
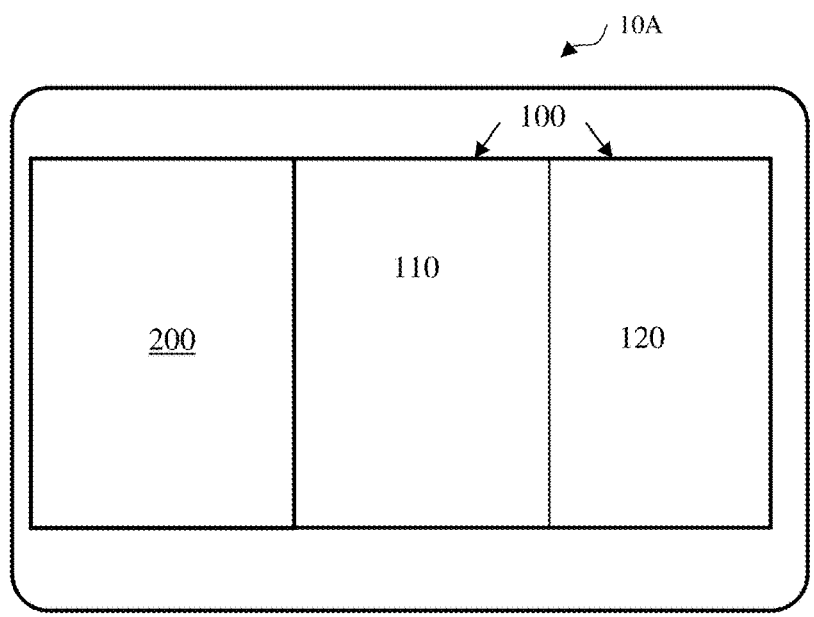
FIG. 2 is a plan view of one embodiment of a multi-tiered health isolation facility.

Referring to FIG. 2, one embodiment of an isolation facility 10A includes a medical staff facility 200 and a patient facility 100. The patient facility 100 includes a suspected contagious (infectious) patient facility 110 and a contagious (infectious) patient facility 120. Within the suspected contagious patient facility 110, patients can be evaluated and can be isolated from other suspected patients in separate rooms.

Figure 3:
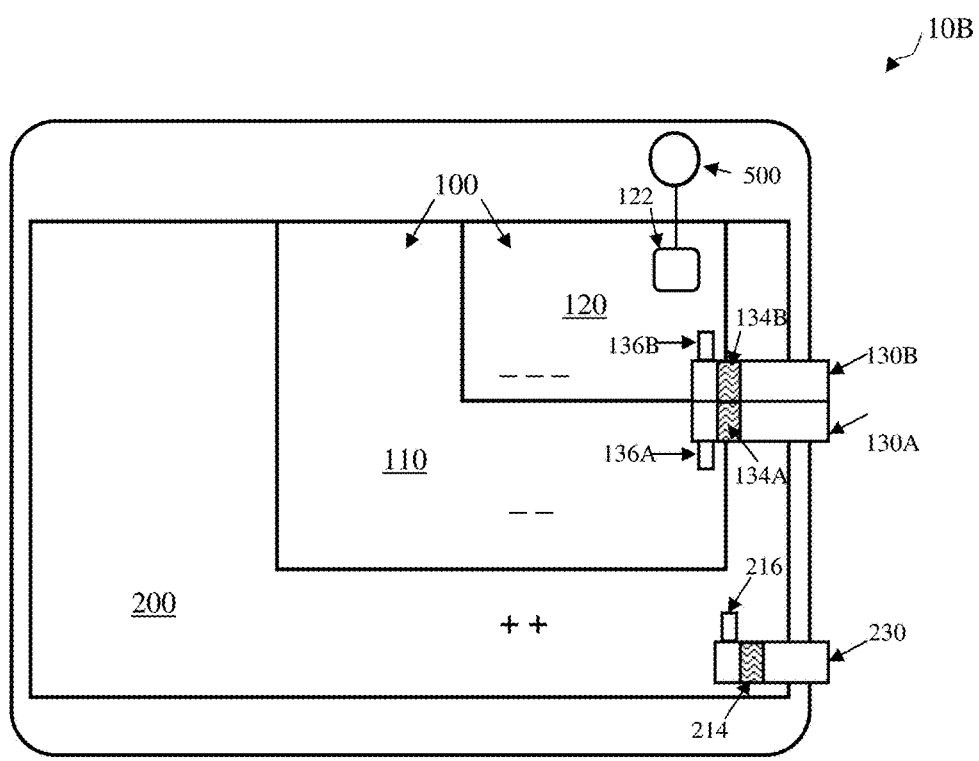
FIG. 3 a plan view of perspective cut-away view of the patient facility of the present invention.

Referring to FIG. 3, another embodiment of a tiered heath isolation facility 10B is illustrated. The facility 10B, includes a medical staff facility 200. Within this medical staff facility 200 is nested a patient facility 100. The patient facility can include a suspected contagious patient facility 110 and an infectious patient facility 120 for patients known to be contagious. The suspected contagious patient facility 110 is kept at a negative pressure differential relative to the medical staff facility 200 and thereby there should be no airflow from the suspected contagious patient facility 110 to the medical staff facility 200.

Also shown in FIG. 3 are plus signs "+" and minus signs "−". These are used to show the relative pressures within each facility type. The "++" for the medical staff facility 200 indicates the highest pressure relative to the patent facility types 110, 120 and a positive pressure relative to atmospheric pressure. As discussed above, the positive air pressure relative to the patient facility 100 prevents leakage of patient facility 100 air, potentially containing airborne contagions, from entering the medical staff facility 200. The "−−" within the suspected contagious patient facility 110 indicates a negative pressure differential relative to the medical staff facility 200. The "−−−" within the contagious patient facility 120 indicates a pressure lower than the pressure within the adjacent suspected contagious patient facility 110.

The medical staff facility also includes a ventilation system 230 that provides the means to provide positive pressurization of the medical facility 200 and the recirculation and replacement of air within the medical facility 200. The ventilation system 230 includes a HEPA filter 214 that filters out the airborne contagions. The ventilation system can further include an ultraviolet light 216 configured to neutralize any contagions that make it through the HEPA filter 214. Preferably, the ventilation system 230 flow-rate is sufficient to filter the medical facility's 200 air a minimum of twelve times per hour. Additionally, the medical staff facility 200 ventilation system 230 is separated from the patient's ventilation systems 130A, 130B. Given that the patient facility 100 could have a large amount of airborne contagions, a failure of the filtering system could infect all the unprotected medical personal within the medical staff facility 200.

The patient facility 100 can include one or more facility types including one for evaluating whether a patient is contagious 110, and one for patients determined to be ill and contagious 120.

A ventilation system 130A is shown coupled to the suspected patient facility 110. This ventilation system 130A can be a separate system or part of a system that provides ventilation for the entire patient facility 100. The ventilation system 130A is configured to produce a negative pressure differential between the medical staff facility 200 and suspected contagious patient facility 110. The means for producing a negative pressure differential includes blowers, fans, pumps or any other means known in the arts for generating a negative pressure differential. One skilled in the art of building semiconductor clean rooms or medical isolation rooms would be skilled in selecting and designing equipment for this task. Further, the ventilation system 130A is configured with a HEPA filter 134A to filter out airborne contagions. Also, the ventilation system 130A can include an ultraviolet light 136A to neutralize any contagions that make it past the HEPA filter 134A. The ventilation system 130A is also configured for a higher air changes per hour (ACH) rate than for the medical staff facility 200. Preferably, the ACH rate is between twelve to twenty times per hour.

The contagious (infectious) patient facility 120 includes a ventilation system 130B that can be part an overall patient facility 100 ventilation system 130A, 130B or a separate ventilation system 130B for the contagious (infectious) patients facility 120. The ventilation system 130B is configured to produce a negative pressure differential between the contagious (infectious) patient facility 120 and the suspected patient facility 110. Further, the ventilation system 130A is configured with a HEPA filter 134B to filter out airborne contagions. Also, the ventilation system 130B can include an ultraviolet light 136B to neutralize any contagions that make it past the HEPA filter 134A. The ventilation system 130A is also configured for a higher ACH rate than for the suspected patient facility 110. Preferably, the ACH rate is greater than twenty times per hour.

The contagious (infectious) patient facility 120 can include a toilet 122. The waste generated by the toilet can be connected to a waste management system 500. The waste generated by contagious (infectious) patients can present a risk to the public and surrounding environment if not neutralized. In one embodiment the waste management system 500 autoclaves or hydroclaves the contents eliminating any biological hazard.

Figure 4:
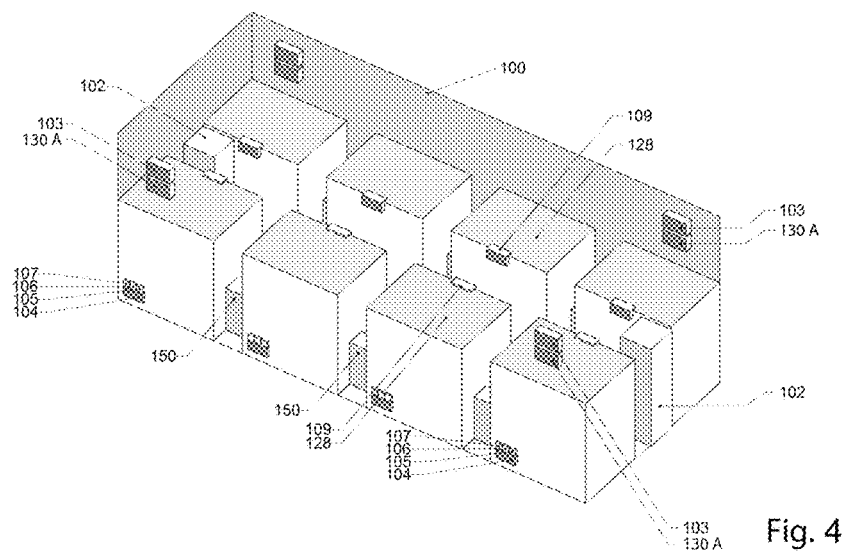
FIG. 4 is a perspective view of one embodiment of a patient facility of the present invention.

Referring to FIG. 4, there is shown a perspective cut-away view of a patient facility 100. The patient facility 100 can be coupled to other facilities types including but not limited to a medical staff facility 200, medical staff personal protective equipment (PPE), an anteroom, a personal protective equipment (PPE) donning facility, a personal protective equipment (PPE) doffing facility, infected patient transportation facility, a laboratory facility.

In the shown embodiment of the patient facility 100, the facility has entry door with airlock 102, an air intake vent 103, an air exhaust vent 104 from an individual patient isolation facility, an optional electrical connection 105, an optional water connection 106, an optional sewer connection 107, an individual patient isolation facility 128, an air intake vent 109 into an individual patient isolation facility, an air contamination abatement system 150.

Figure 5:
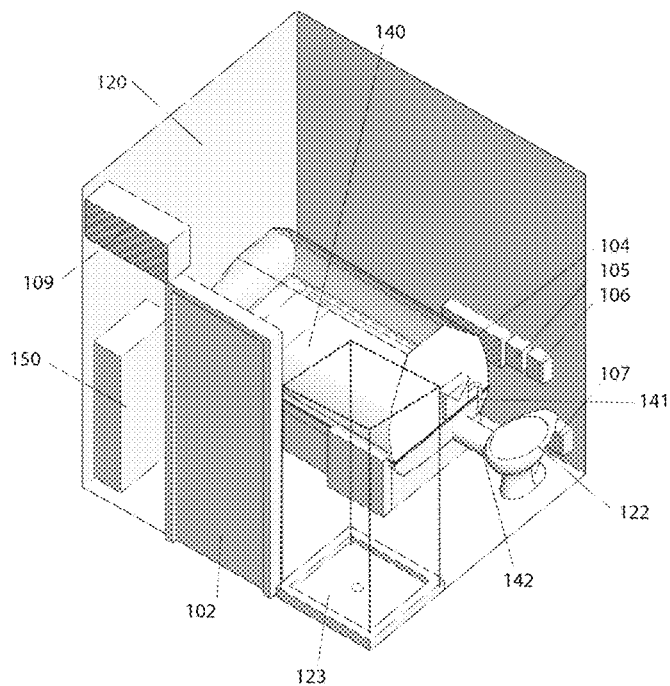
FIG. 5 is a is a perspective cut-away view of an individual patient isolation facility including an individual patient isolation transport facility.

Referring to FIG. 5, there is shown a perspective cut-away view of an individual patient isolation facility 120 including an individual patient isolation transport facility 140, an optional toilet 122, an optional shower 123, an air exhaust vent 104, an optional electrical connection 105, an optional water connection 106, an optional sewer connection 107, an entry door 102, an air intake vent 109, and an air contamination abatement system 150, a blower hose 141, and a snorkel port 142.

All or part of the patient isolation facility shown in figure five can be contained within a mobile vehicle including but not limited to an patient isolation ambulance, boat or truck. Features such as a shower or toilet would not be needed. The same principles would apply with negative pressures being used to protect leakage of contagions into areas where personal might not be protected including but not limited to a driver.

Those skilled in the relevant art will recognize that many changes can be made to the embodiment described, while still attaining the beneficial results of the present invention. It will also be apparent that some of the desired benefits of the present invention can be attained by selecting some of the features of the present invention without utilizing other features. Accordingly, those skilled in the art will recognize that many modifications and adaptations to the present invention are possible and can even be desirable in certain circumstances, and are a part of the present invention. Thus, the previous is provided as illustrative of the principles of the present invention and not a limitation thereof.

What is claimed is:

1. A multi-tiered health isolation facility comprising:
   a plurality of facility types in a multi-tiered configuration to form a nested patient isolation facility,
   wherein each of the plurality of facility types is connected to one or more of the other plurality of facility types, wherein each facility type has a probability of containing an airborne infectious contagion,
   wherein a negative air-pressure differential is provided between each of the plurality of facility type having a higher probability of airborne infectious contagions and a facility type having a lower probability airborne infectious contagions,
   wherein the negative air-pressure differential is configured to prevent movement of airborne infectious contagions based on preventing leakage of air from each of the plurality of facility types having the higher probability of airborne infectious contagions, and
   wherein the facility types comprise a contagious (infectious) patient facility and a suspected contagious patient facility, with the contagious patient facility nested within the suspected contagious patient facility and configured with a relatively higher negative air-pressure within the nested contagious patient facility.

2. The isolation facility of claim 1, further comprising;
   a ventilation system associated with each of the plurality of facility type, wherein each ventilation system has an associated air change flow and air changes per hour (ACH) rate, and wherein the air changes per hour (ACH) rate is higher in the facility type with a higher probability of airborne infectious contagion than the facility type with a lower probability of having airborne infectious contagion.

3. The isolation facility of claim 2, wherein one of the plurality of facility types is a medical staff facility wherein the medical staff facility has the lowest probability of airborne infectious contagion.

4. The isolation facility of claim 3, wherein the associated ventilation system of the medical staff facility is configured to provide a positive pressure relative to the adjacent facility types and the ambient atmosphere pressure.

5. The isolation facility of claim 3, wherein each of the associated ventilation system has a HEPA filter.

6. The isolation facility of claim 5, further comprising;
   one or more ventilation system duct works associated with the one or more ventilation systems; and
   one or more ultraviolet sterilization systems configured to process air passing through the one or more ventilation system duct works.

7. The isolation facility of claim 6, wherein the ventilation system associated with the medical staff facility is not connected with the ventilation systems associated with other plurality of facility type.

8. The isolation system of claim 7, further comprising one or more exhaust HEPA filters associated with one or more of the ventilation systems wherein each of the ventilation system is coupled to the external environment, wherein a portion of the associated air changes per hour (ACH) flow is exhausted to the external environment forming an associated exhaust flow, and wherein the one or more exhaust flows are filtered by the associated one or more HEPA filters.

9. The isolation facility of claim 8, wherein the associated ventilation system changes the air within the suspected contagious patient facility 12-20 times an hour.

10. The isolation facility of claim 8, wherein the associated ventilation system changes the air within the contagious patient facility more than 20 times an hour.

11. The isolation facility of claim 8, further comprising a bathroom containing one or more of a toilet, shower, bathtub, and sink; and
a waste water incinerator or waste water sterilizer, wherein the bathroom is within the contagious (infectious) patient facility, and wherein the one or more of the toilet, the shower, the bathtub, and the sink are connected to the waste water incinerator.

12. The isolation facility of claim 8, wherein the contagious (infectious) patient facility is configured to hold one or more patients.

13. The isolation facility of claim 1, wherein the plurality of facility types are mobile and part of a mobile vehicle.

14. The isolation facility of claim 13, wherein the mobile vehicle is an ambulance.

15. A multi-tiered health isolation facility comprising:
a plurality of facility types in a multi-tiered configuration to form a nested patient isolation facility,
wherein each of the plurality of facility types is connected to one or more of the other plurality of facility types, wherein each facility type has a probability of containing airborne infectious material,
wherein a negative air-pressure differential is provided between
each of the plurality of facility type having a higher probability of airborne infectious material and a facility type having a lower probability airborne infectious material, wherein the negative air-pressure differential is configured to prevent movement of airborne infectious contagions based on preventing leakage of air from each of the plurality of facilities types having the higher probability of airborne infectious contagions, and
wherein the facility types comprise a contagious (infectious) patient facility and a suspected contagious patient facility, with the contagious patient facility nested within the suspected contagious patient facility and configured with a relatively higher negative air-pressure within the nested contagious patient facility;
a ventilation system associated with each of the plurality of facility type, when each ventilation system has an associated air change flow and an air
changes per hour (ACH) rate, and wherein the air changes per hour (ACH) rate is higher in the facility type with a higher probability of airborne infectious material than the facility type with a lower probability of having airborne infectious material;
one or more exhaust HEPA filters associated with one or more of the ventilation systems wherein each of the ventilation system is coupled to the external environment, wherein a portion of the associated air changes per hour (ACH) flow is exhausted to the external environment forming an associated exhaust flow, and
wherein the one or more exhaust flows are filtered by the associated one or more HEPA filters;
one or more ventilation system duct works associated with the one or more ventilation systems; and
one or more ultraviolet sterilization systems configured to process air passing through the one or more ventilation system duct works,
wherein one of the plurality of facility types is a medical staff facility wherein the medical staff facility has the lowest probability of airborne infectious material,
wherein the associated ventilation system of the medical staff facility is configured to provide a positive pressure relative to the ambient atmosphere pressure,
wherein each ventilation system has a HEPA filter,
wherein the ventilation system associated with the medical staff facility is not connected with the ventilation systems associated with other plurality of facility types.

16. A multi-tiered health isolation facility comprising:
an individual patient isolation transport facility;
a contagious (infectious) patient isolation facility; and
a medical staff facility,
wherein the multi-tiered health isolation facility forms a nested health isolation facility,
wherein in the nested health isolation facility comprises the individual patient isolation transport facility within the contagious (infectious) patient isolation facility and the contagious (infectious) patient isolation facility within the medical staff facility,
wherein a negative air-pressure differential is provided between the patient isolation transport facility, and a negative air-pressure differential is provided between the contagious (infectious) patient isolation facility and the medical staff facility, and wherein the negative air-pressure differential is configured to prevent movement of airborne contagious based on preventing leakage of air from the patient isolation facility to the medical staff facility, and
wherein nested health isolation facility comprises a contagious (infectious) patient facility and a suspected contagious patient facility, with the contagious patient facility nested within the suspected contagious patient facility and configured with a relatively higher negative air-pressure within the nested contagious patient facility.

17. The isolation facility of claim 16, further comprising;
an individual patient isolation transport facility ventilation system,
an contagious patient isolation facility ventilation system, and
a medical staff ventilation system facility, wherein the individual patient isolation transport facility ventilation system air changes per hour (ACH) rate is higher than the contagious patient isolation facility ventilations system air changes per hour, which is higher than the medical staff ventilation system facility ventilation system air changes per hour.

* * * * *